Figure 1:
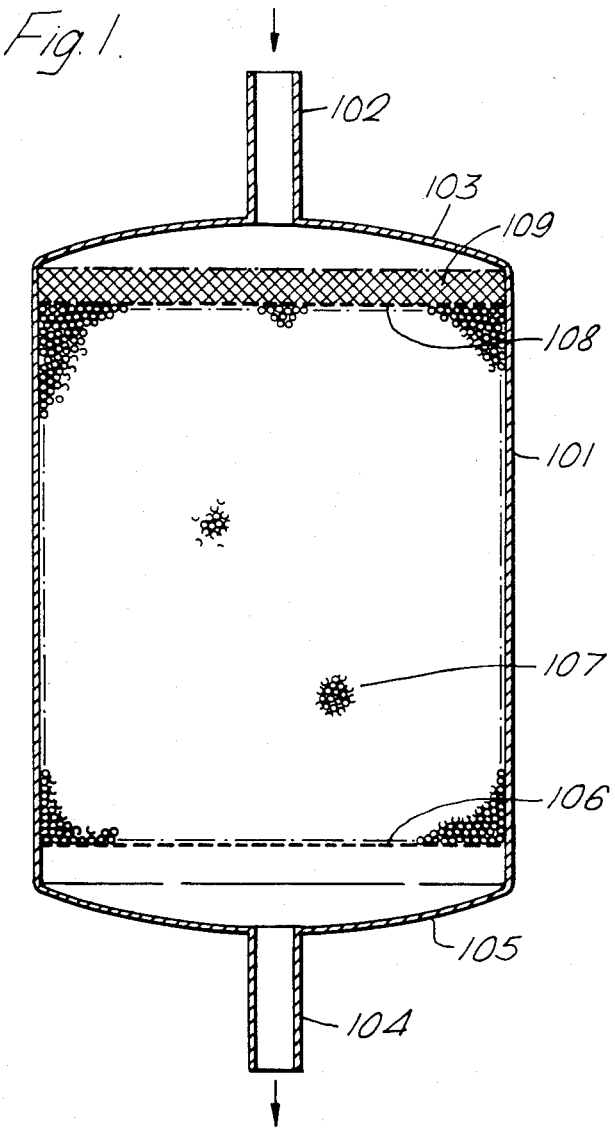

United States Patent [19]

Gani et al.

[11] Patent Number: 4,490,290

[45] Date of Patent: Dec. 25, 1984

[54] PROCESS FOR THE RECOVERY OF IMMUNOGLOBULINS

[75] Inventors: Mohamed M. Gani, Bedfordshire; Keith May; Philip Porter, both of Bedford, all of England

[73] Assignee: Internationale Octrooi Maatschappij "Octropa" B.V., Rotterdam, Netherlands

[21] Appl. No.: 425,099

[22] PCT Filed: Feb. 24, 1982

[86] PCT No.: PCT/GB82/00060
§ 371 Date: Sep. 22, 1982
§ 102(e) Date: Sep. 22, 1982

[87] PCT Pub. No.: WO82/02818
PCT Pub. Date: Sep. 2, 1982

[30] Foreign Application Priority Data

Feb. 26, 1981 [GB] United Kingdom ............... 8106099

[51] Int. Cl.³ .......................... A61K 35/16; A23J 1/20
[52] U.S. Cl. ........................... 260/112 B; 260/120; 260/112 R; 435/68; 435/948; 424/85; 424/101; 210/679; 210/927
[58] Field of Search ............... 260/112 R, 112 B, 119, 260/120; 435/68, 948; 424/85, 177, 101

[56] References Cited

U.S. PATENT DOCUMENTS

| 3,553,317 | 1/1971 | Michealson et al. | 260/112 R |
|---|---|---|---|
| 3,652,761 | 3/1972 | Weetall | 260/112 |
| 4,229,342 | 10/1980 | Mirabel | 260/120 |
| 4,256,631 | 3/1981 | Yokoo | 424/177 |
| 4,384,954 | 5/1983 | Nakashima et al. | 260/112 B |
| 4,409,105 | 10/1983 | Hayashi et al. | 260/112 B |
| 4,436,658 | 3/1984 | Peyrouset et al. | 260/112 R |

FOREIGN PATENT DOCUMENTS

| 2319399 | 2/1977 | France . |
| 2403556 | 4/1979 | France . |
| 2451745 | 10/1980 | France . |
| 1544867 | 4/1979 | United Kingdom . |
| 2004892 | 4/1979 | United Kingdom . |
| 2044775 | 10/1980 | United Kingdom . |

OTHER PUBLICATIONS

Chemical Abstract, No. 97: 158992–Agarose polyacrolein Microsphere beads, New Effective Immunoabsorbent, 1982.
Y

*Primary Examiner*—John Kight
*Assistant Examiner*—Garnette D. Draper
*Attorney, Agent, or Firm*—Cushman, Darby & Cushman

[57] ABSTRACT

A process for the recovery of immunoglobulins of high purity and potency from milk, in which process milk is passed through a re-usable immunoadsorbent column comprising an insoluble carrier material to which is bound a low-affinity monoclonal antibody specific to one or more milk immunoglobulins but not specific to any other common constituent of milk, the antibody bind immunoglobulin molecules are released by eluting the immunoadsorbent.

6 Claims, 3 Drawing Figures

PROCESS FOR THE RECOVERY OF IMMUNOGLOBULINS

The present invention relates to the recovery of materials.

In particular the invention relates to methods for recovering immunoglobulins from sources such as milk and blood serum. In this specification, the term "milk" is used to mean whole milk or any derivative of whole milk, such as skimmed milk or whey, in liquid or in solid form so long as such solid form is soluble or dispersible in water, the whole milk or derivative thereof containing biologically active immunoglobulins.

The recovery of immunoglobulins from so-called "immune milk" is desirable because the recovered immunoglobulins have valuable biologic function in providing antibody protection. Appropriate immunoglobulins can be fed to or injected into disease-susceptible humans or animals to provide therapeutic and/or prophylactic benefits. The recovered immunoglobulins can also be used as valuable research tools in the understanding of immune responses against diseases, and they can also form the basis of immunodiagnostic test procedures.

Milk, especially bovine milk, is a particularly important natural source of immunoglobulins. Mammals such as the cow can be immunised successfully against a wide variety of diseases.

Examples of disease-causing organisms against which antibodies can be raised are bacteria such as *E.coli*, Salmonella, Shigella and Cholera; viruses such as *rotavirus* and polio; fungi such as Chlamydia and Candida; protozoa such as Giardia; helminths and liver flukes.

Another important source of immunoglobulins is blood. For example anti-tetanus immunoglobulins can be obtained from horse blood.

Methods have previously been proposed for recovering immunoglobulins from immune bovine milk, but these prior methods have involved the use of techniques such as filtration and ultrafiltration to produce a concentrated residue from the original milk containing the desired immunoglobulins. In such a process the bulk of the milk has to be discarded and wasted, and the concentrated residue, while containing the valuable immunoglobulins, also contains concentrated quantities of numerous other trace ingredients in the original milk. Many of these trace ingredients are undesirable in such high concentrations. Furthermore, such processing usually reduces the potency of the immunoglobulins because they can all too easily be denatured under severe processing conditions.

There is therefore a need for a process that enables valuable immunoglobulins of high potency to be extracted economically from sources such as milk without the need to discard the bulk of the original material and without the disadvantage of simultaneously concentrating other minor ingredients present in the original material. Ideally, such a process would have two end products; the first being pure concentrated immunoglobulins and the second being the original source deficient solely in respect of the immunoglobulins. Immunoglobulins of high purity are especially important where they are to be employed in injectable form.

Of particular interest are the immunoglobulins of classes IgA, IgM, IgG and IgE.

The invention provides a process for the recovery of immunoglobulins wherein a source of immunoglobulins is contacted with an insoluble carrier material to which is bound a low-affinity antibody specific to one or more of the immunoglobulins but not specific to any other common constituent of the source, the antibody binds immunoglobulin molecules, and following removal of the residue of the source the immunoglobulin molecules are released from the antibody.

In a preferred embodiment, the invention provides a process for the recovery of immunoglobulins of high purity and potency from milk, in which process milk is contacted with an insoluble carrier material to which is bound a low-affinity antibody specific to one or more milk immunoglobulins but not specific to any other common constituent of milk, the antibody binds immunoglobulin molecules, and following removal of the residue of the milk the immunoglobulin molecules are released from the antibody.

A further embodiment of the invention is an apparatus for recovering from milk immunoglobulins of high purity and potency, comprising an immunoadsorbent column or filter through which milk can be passed, the immunoadsorbent column or filter comprising a low-affinity antibody specific to one or more milk immunoglobulins but not specific to any other common constituent of milk, the antibody being immobilised on an insoluble carrier material, and means for eluting the immunoadsorbent column or filter to release bound immunoglobulin from the antibody. Preferably the apparatus also comprises means for flushing the immunoadsorbent column or filter free of milk prior to elution.

In order to ensure high purity in the recovered immunoglobulins, it is important that the antibody should be one that will specifically bind the immunoglobulin material of interest but which will not bind other materials that normally occur in the source being treated.

In order to preserve their high potency, it is essential that the immunoglobulins must not be significantly denatured during this recovery process. Accordingly, the antibody that is used to extract the immunoglobulins from the source must be one whose affinity for the immunoglobulins is specific but nevertheless sufficiently weak in terms of the bond that is formed between the antibody and the immunoglobulins that it will be comparatively easy to promote subsequent release of the immunoglobulins from the antibody by means of, for example, a minor change in pH or electrolyte concentration.

Examples of suitable eluting agents or mechanisms are:

(a) Media that will cause a change in pH (from near neutral pH at which the bound antibody will be active) down towards 2 or up towards 10 or 11, eg glycine/HCl buffer, aqueous acetic acid, aqueous propionic acid or aqueous ammonia;
(b) media that will cause a decrease in polarity, eg 50% aqueous ethylene glycol or 10% aqueous dioxane;
(c) dissociating agents, eg 6–8M aqueous urea or 6M aqueous guanidine hydrochloride;
(d) choatropic ions (electrolytes), eg sodium iodide, magnesium chloride or sodium thiocyanate, in aqueous solution at suitable molarity; and
(e) electrophoretic desorption.

Following elution of the immunoglobulin from the antibody, it will generally be advisable to separate the immunoglobulin and the eluting agent, for example by means of dialysis, as rapidly as possible. Prolonged exposure of the immunoglobulin to the eluting agent may lead to some denaturation of the immunoglobulin, and so it should be transferred to a physiologically neutral environment.

Preferably, the antibody will be a so-called "monoclonal antibody", that is, an antibody expressed by a permanent cell line derived from a single antibody-producing cell, eg a single mammalian spleen cell. Such permanent cell lines can be obtained, for example, as hybridoma cell lines derived from the fusion of myeloma cells with spleen cells from an animal immunised against the immunoglobulins to which the antibody is specific.

Ideally, in view of the high degree of specificity desired in the antibodies used in the invention, it is preferred that the antibody should recognise only one binding site (determinant) on an immunoglobulin molecule. The antibody can be either an anti-(light chain) antibody or an anti-(heavy chain) antibody. The former will bind specifically either lambda or kappa light chains, but will recover all classes of immunoglobulin having the appropriate light chain. The latter will bind specifically an individual immunoglobulin (e.g. bovine $IgG_1$) or a number of immunoglobulins possessing a common determinant on their characterising heavy chains.

In a preferred embodiment of the invention, the removal of the immunoglobulins can be accomplished while the source in liquid form is flowing past or through a bed of insoluble carrier material loaded with the antibody. For example, the liquid can be passed through a column packed with the carrier material. The carrier material should have a relatively large surface area, and carrier materials in the form of small beads, net, or mesh, are ideal.

The chemical nature of the carrier material itself is not critical to the invention, and indeed a wide variety of suitable carriers are known in the art because many techniques for insolubilising biologically active proteinaceous agents, such as enzymes, have been described in the scientific literature. Many suitable carriers are available commercially. The carrier material (often referred to in the art as a matrix) can be nylon, agarose, cellulose, polystyrene, polyacrylamide, carbon fibre, glass, paper, latex or indeed any material that provides immobilisation of the antibody while at least substantially retaining the desired antigen-binding and antigen release characteristics of the antibody. Under the normal conditions of use, the carrier material should be non-degradable, to reduce the risk of bacterial growth and contamination.

A wide variety of chemical techniques are available for linking biologically active proteins to carrier materials. The chemical structure of some matrices already contain suitable functional groups, and such groups can be used in the coupling reaction or can be modified if desired. For other matrices, which do not inherently contain suitable functional groups, techniques are available for introducing such groups. Functional groups generally require activation, for which a variety of mechanisms are available.

For example, acid hydrolysis of nylon yields abundant free carboxyl (—COOH) and amino (—$NH_2$) groups which can be used for protein linkage. The carboxyl groups can be activated using, for example, N-hydroxy succinamide esters or N-carbodiimides. The amino groups can be activated with glutaraldehyde or cyanogen bromide, for example. Polysaccharides, such as agarose or cellulose, naturally contain hydroxyl (—OH) groups, which can be activated using for example, cyanogen bromide or periodate oxidation. Polystyrene and polyacrylamide do not inherently contain any suitable functional groups, but such groups can readily be introduced. For example, amino groups can be introduced in polystyrene by nitration and reduction. Following introduction, the amino groups can be activated using the procedures adopted for nylon, or if desired can be converted to other functional groups such as hydroxyl. Glass can be silylated using commercially available reagents, which generally provide amino groups which can be activated as already described.

By way of example only, a particularly preferred embodiment of the invention will now be described in greater detail.

Recovery of immunoglobulins from milk

Immune bovine milk contains substantial quantities of the immunoglobulin $IgG_1$, which for example could usefully be added to synthetic foodstuffs such as dried milks and milk substitutes for human and animal consumption to provide passive immunity against infections such as gastroenteric diseases.

A monoclonal antibody specific to $IgG_1$ can be produced by techniques that are in principle already well known. A typical procedure will involve injecting purified $IgG_1$, typically isolated by ion exchange chromatography on DEAE cellulose (a procedure that has yielded sufficient quantities of pure immunoglobulins for research purposes but which is wholly uneconomic as a commerical process) into a host animal, such as a "germfree"mouse, to cause the host spleen cells to generate antibodies. The host animal is then killed, and the spleen removed to yield free spleen cells. These cells are encouraged to fuse with myeloma cells using a standard reagent, such a polyethylene glycol, to give hybridoma cells expressing the antibodies. Cell lines expressing anti-$IgG_1$ are screened by immunochemical assay, cultured in vitro or in vivo and then selected for their relative affinity by studying their elution characteristics from conveniently insolubilised bovine $IgG_1$.

Cell lines expressing the selected monoclonal antibodies are cultured further, the expressed antibody fraction purified by chemical means or preferably by an elution procedure analogous to that employed in the affinity selection test and the antibody bound to a solid support system. This immunoadsorbent can be packed into a column, for example.

An immunoadsorbent-containing column is incorporated in a conventional milk processing unit such that at least a substantial proportion of the milk throughput of the unit passes through the column. It is common practice to incorporate filters, made for example from nylon, paper or cotton, in milk processing lines and such a filter can be adapted to the purpose of the invention. Preferably, however, the immunoadsorbent of the invention is placed downstream from the standard milk filter. At appropriate intervals, when the antibody on the immunoadsorbent has become saturated with immunoglobulin, the immunoadsorbent column or filter is replaced and the immunoglobulin is recovered from the saturated immunoadsorbent, which is then ready for re-use.

The immunoadsorbent column or filter can be an integral part of a milk processing line, or it can be utilised as a peripheral processing feature. Complications may arise in the former situation if the flow of milk through the column or filter impedes the general flow rate through the line. For example, heat exchangers commonly employed in milk pasteurisation or sterilisation require a rapid and uninterrupted flow of milk if the risk of overheating and burning is to be avoided. This may be inconsistent with the optimum flow conditions through an immunoadsorbent column or filter, where slow flow through a tightly-packed carrier material may be more efficient. For an "in-line" arrangement a balance may need to be struck between efficiency of immunoglobulin recovery and throughout of the milk processing plant as a whole. An alternative arrangement avoiding this possible conflict would be to incorporate the immunoadsorbent column or filter in a recirculation system associated with a bulk holding tank, so that immunoglobulin is recovered from the milk before the milk is passed to the conventional processing line. A further alternative is to pump milk from one bulk tank to another, with the immunoadsorbent column or filter as an intervening stage through which the milk passes en route.

In any arrangement, it will be advantageous to utilise two or more immunoadsorbent columns or filters in parallel. Thus, for example, while one column or filter is being used to extract immunoglobulin from milk, another can be eluted to recover previously-adsorbed immunoglobulin. The milk flow can then be diverted from the first column or filter to the second when the first column or filter has become saturated with immunoglobulin.

To avoid the need for readily-replaceable columns or filter elements, each immunoadsorbent column or filter can be provided with means for elution. Preferably, means is also provided for flushing each column or filter free of residual milk prior to elution and, ideally, free of eluting medium prior to further contact with milk. The flushing medium should be a physiologically innocuous liquid, such as dilute aqueous saline solution or phosphate buffered saline (PBS) that will neither harm the immunoadsorbent nor lead to dangerous contamination if any trace amount is carried through into the milk line.

By means of this process not only can the high concentrations of antibody in colostrum (first milk) be recovered quickly and conveniently, but also the comparatively minor amounts of immunoglobulins that are present in normal bovine milk can be recovered economically.

Immunoglobulins normally comprise much less than 1% of the total protein in bovine milk, for example, so the specificity of the recovery mechanism of the invention leads to removal of the valuable antigenic material leaving the composition of the original natural source material virtually unchanged. In particular, the nutritional properties of milk to which the invention has been applied are essentially unchanged, and the processed milk can be used as a human or animal foodstuff in the normal way.

The effectiveness of the invention is illustrated by the following experimental procedure.

EXPERIMENTAL DEMONSTRATION OF THE INVENTION

(a) Preparation of primed splenocytes

Balb/c mice were immunised intraperitoneally with purified bovine $IgG_1$ followed by booster injections on days 42, 54 and 61. They also received intravenously a booster 3 days before cell fusion. The mice were sacrificed and spleen cells prepared aseptically by removing the spleen and teasing the cells into saline. The cell suspension was then centrifuged at $200 \times g$ for 5 minutes and the pellet resuspended in saline at $10^7$ cells per ml. These steps were carried out at room temperature.

(b) Preparation of Myeloma Cells for Fusion

Balb/c myeloma cells (P3×63.Ag8, available commercially from Flow Laboratories) deficient in hypoxanthine guanine phosphoribosyl transferase (HGPRT) were maintained on Dulbecco's modified Eagle's medium (DMEM) containing 10% foetal calf serum and 10% horse serum. The growth of the line can be inhibited by hypoxanthine, aminopterine, thymidine medium (HAT). On the day of fusion, the myeloma cell suspensions were centrifuged at $200 \times g$ for 5 minutes, the pellet resuspended in saline, centrifuged for 5 minutes at $200 \times g$ and finally suspended in saline at a concentration of $10^7$ cells/ml.

(c) Preparation of Peritoneal Macrophages

On the day before fusion, 3 Balb/c mice were killed, the abdominal skin removed and 4–5 ml saline injected peritoneally, entering directly above the symphysis and letting the tip of the needle rest over the right lobe of the liver. After gentle massage of the abdomen the fluid was withdrawn, yielding $1-3 \times 10^6$ macrophages per mouse. The cells were collected in polypropylene tubes, washed with the DMEM, pooled and counted, then centrifuged for 5 minutes, at $200 \times g$ and resuspended in HAT at $5 \times 10^5$ cells/ml. The cells were distributed at $2-3 \times 10^4$ cells per cup in Linbro plates and left in a 6% $CO_2$ incubator to be ready for use next day.

(d) Fusion

For fusion, $2 \times 10^7$ spleen cells were combined with $5 \times 10^7$ myeloma cells and the suspension centrifuged at $200 \times g$ for 5 minutes. The supernatant was discarded and the pellet loosened. Then to the pellet 1.0 ml of 50% solution (w/v) of polyethylene glycol (PEG) 3000 or 0.2 ml of 35% solution (w/v) of PEG 1500 was added. The cells were incubated for 1 minute, under constant agitation at room temperature followed by immersion for 2 minutes, without agitation in a 37° C. water bath. The fusion was stopped by slowly adding 20 ml saline over the next 5 minutes. The cells were centrifuged for 5 minutes at $200 \times g$. The supernatant was discarded and the pellet gently resuspended in HAT. The cells were then distributed at $7 \times 10^4$ (spleen) concentration per cup in the pre-treated Linbro plates. The plates were incubated at 37° C. in a 6% $CO_2$ incubator.

(e) Maintenance

Cultures were inspected on days 4, 7, 10 and then every other day, up to the end of the third week. On each of these days, 1 ml of medium was removed by suction and replaced by fresh HAT medium up to day 21, and then by normal growth medium thereafter. The supernatant from wells containing more than $10^4$ hybrid cells was tested for antibodies to the bovine $IgG_1$ using an enzyme-linked immunoassay. The positive clones were then transferred to a 25 cc flask containing 2 ml fresh medium. As soon as the hybrids has grown almost to confluence in the 25 cc flasks, the cells were preserved by being frozen in 10% DMSO.

(f) Antibody production

Samples of the preserved clones were injected into pristane-treated mice. Ascitic fluid was collected from these mice after 15 days. The fluid contained approximately 3 mg per ml of the specific monoclonal antibody.

(g) Selection of antibodies

The suitability of the anti-(bovine IgG₁) antibodies for the purposes of the invention was assessed by passing ascitic fluid containing the antibody down a column containing bovine IgG₁ bound to cyanogen bromide activated sepharose. After the column had been washed free of ascitic fluid using PBS, it was eluted with aqueous $MgCl_2$ solutions of increasing molarity in the range 0 to 5M, at room temperature, and the eluate tested for the presence of antibody. Any antibody that is released at a molarity of less than 5M possesses an affinity for bovine $IgG_1$ that is sufficiently weak that the antibody can form the basis of a method for selectively and recoverably extracting $IgG_1$ from immune bovine milk.

(h) Recovery of immunoglobulin from bovine milk 15 mg of antibody that was released at a molarity of 4M $MgCl_2$ was bound to 0.5 gm of cyanogen bromide activated sepharose, packed into a column, and the column was eluted with immune bovine milk. After washing with PBS and elution with 4M aqueous $MgCl_2$, a yield of 3 mg $IgG_1$ was recovered.

The recovery procedure was repeated 10 times using the same column, with a yield of about 3 mg $IgG_1$ being obtained on each occasion. This indicated that the column had an extraction capacity of about 3 mg $IgG_1$, which is very reasonable having regard to factors such as steric hindrence which will reduce the efficiency of the immunoadsorbent. It also clearly demonstrates the re-usable nature of the immunoadsorbent. Normal bovine milk typically has an $IgG_1$ content of about 0.5 mg/ml, so the immunoadsorbent had the capacity to extract all of the $IgG_1$ from 5–6 ml of milk per run.

The column was maintained at 4° C. for over one year, during which period it was used more than 100 times, with consistent yields of recovered immunoglobulin, thus further demonstrating the re-usability of the column.

IN VITRO CULTIVATION OF ANTIBODIES

Anti-bovine IgG monoclonal antibodies raised by the above technique can be produced in quantity by in vitro cultivation of hybrid cell lines. In vitro cultivation can yield substantial (eg kilogram) quantites of antibody and enables commercial-scale immunoadsorbent apparatus to be manufactured.

ASSAY FOR BIOLOGICAL ACTIVITY OF RECOVERED IMMUNOGLOBULINS

(a) Anti-haemolysin activity

Serial dilutions of immunoglobulin preparations were added to a standard amount of a haemolysin preparation. Sheep red blood cells were then added. Lysis indicated that no immunoglobulin was present whereas a button of cells showed that sufficient immunoglobulin was conducted using milk and bovine blood serum, with the following results.

| Titre | |
|---|---|
| Milk | |
| Original | 1/1000 |
| Fall through from monoclonal antibody immunoadsorbent | 1/640 |
| 1M $MgCl_2$ elution peak | 1/640 |
| *-continued* | |
| Titre | |
| Serum | |
| Original | 1/2000 |
| Fall through | 1/640 |
| 1 M $MgCl_2$ peak | 1/640 |

(b) Anti-0149 *E.coli* activity

Sheep red blood cells were coated with antigen prepared from heat-killed 0149 *E.coli* by allowing adsorbtion for 30 minutes. The cells were washed and serial dilutions of immunoglobulin preparation were added to a standard volume of cells. Agglutination indicated the presence of immunoglobulin. The immunoglobulin preparations were derived from an ammonium sulphate precipitate of blood serum from cow immunised with 0149 *E.coli*, and the results were as follows.

| Ig preparation | Titre |
|---|---|
| Original serum | 1/32000 |
| Fall through | 1/32000 |
| 1 M $MgCl_2$ peak | 1/400 |
| 1 M $MgCl_2$ peak after re-adsorbtion and elution | 1/400 |

These assays demonstrate that it is possible using the invention to isolate bovine immunoglobulin from milk and serum using a monoclonal immunoadsorbent, with full retention of biological activity.

COMMERCIAL-SCALE RECOVERY OF IMMUNOGLOBULIN

Figure 2:
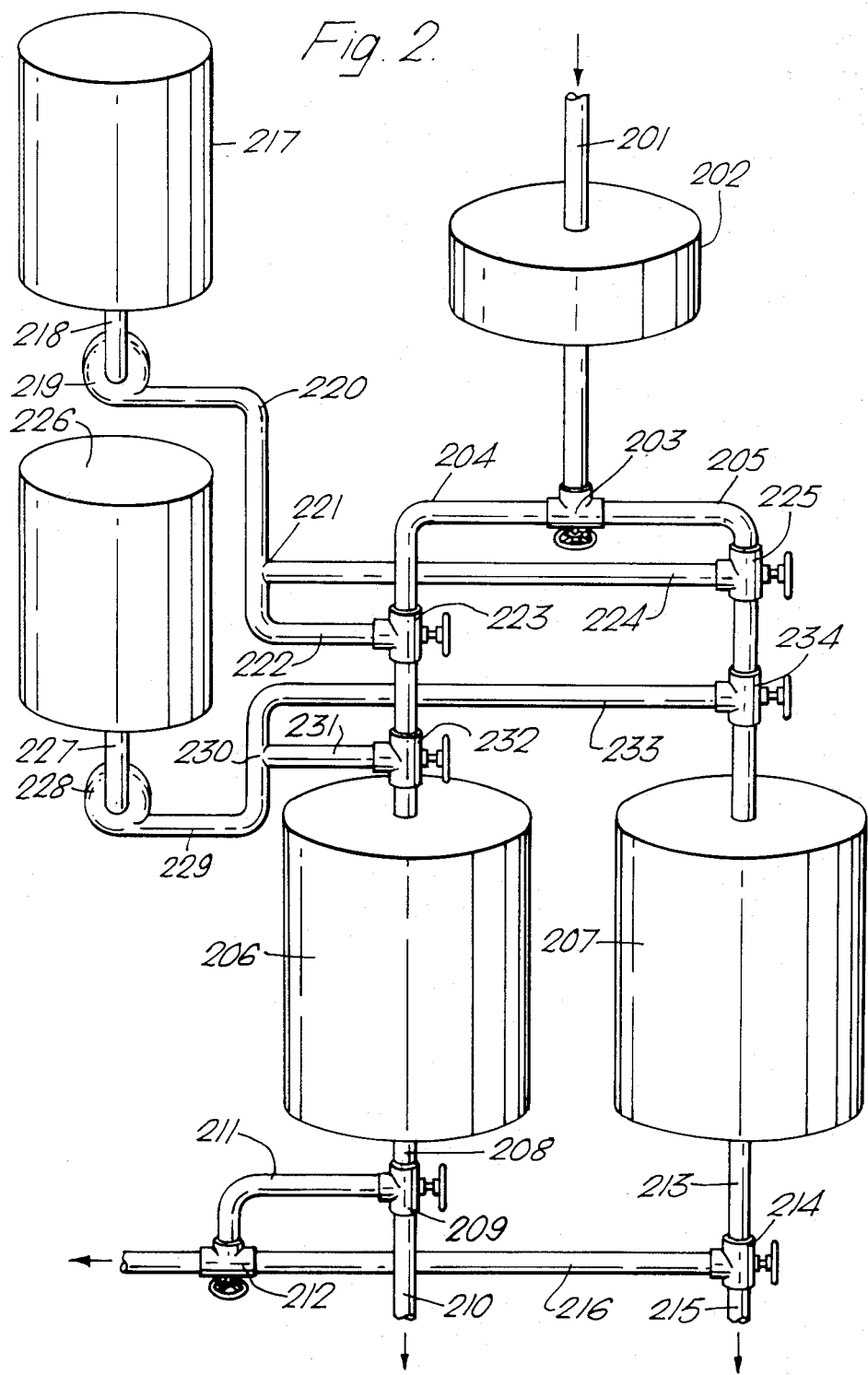
Figure 3:
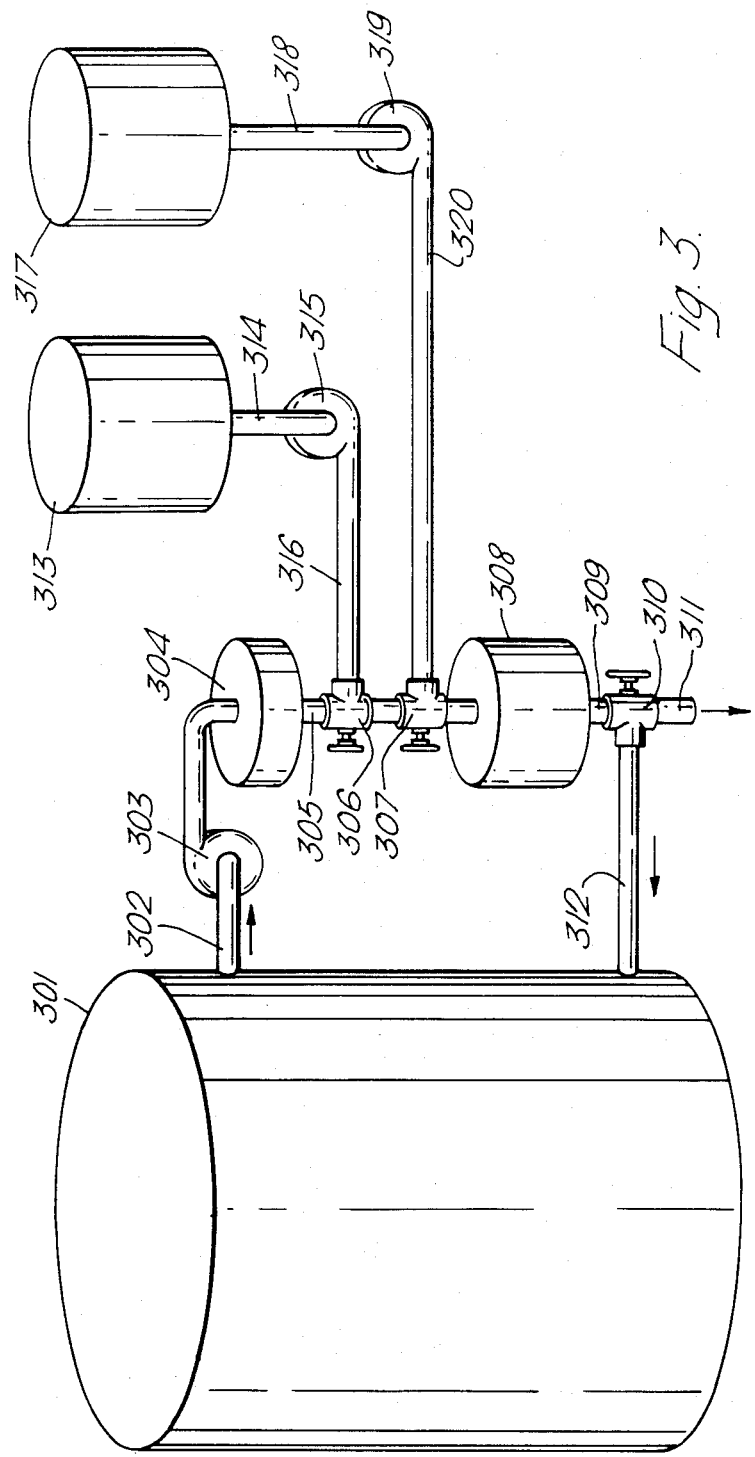

By way of example only, some installations for the commercial scale recovery of immunoglobulins from milk are illustrated in the accompanying drawings, of which FIG. 1 depicts in cross-sectional elevation an immunoadsorbent column in accordance with the invention;

FIG. 2 depicts the general lay-out of a recovery installation involving two immunoadsorbent columns; and FIG. 3 depicts the general lay-out of a recovery system involving recirculation in a bulk tank.

As shown in FIG. 1, the immunoadsorbent column comprises an upright cylindrical vessel 101 with an inlet pipe 102 situated centrally in the top 103 of the vessel and an outlet pipe 104 situated centrally in the floor 105 of the vessel. A foraminous plate 106 is mounted just above floor 105 and spans the entire horizontal cross-section of the vessel. The purpose of the plate 106 is to act as a support for immunoadsorbent material 107, depicted in the form of beads, packed within the body of the vessel 101, and also to prevent particles of immunoadsorbent material being carried through the outlet 104 by any liquid passing through the column. A second foraminous plate 108 is mounted above the immunoadsorbent material 107 and similarly spans the entire horizontal cross-section of the vessel. Plate 108 helps to maintain the immunoadsorbent material in position, and also help to ensure a uniform flow of liquid through the bed of immunoadsorbent material. Above plate 108 is a pre-filter 109 to screen out any solid particles in the liquid that might otherwise become trapped in the immunoadsorbent bed and impede flow.

The vessel 101 can be manufactured from any of the materials normally used in the construction of milk processing equipment. Stainless steel is a good example. If desired, the vessel can be lined with an inert material such as glass.

FIG. 2 illustrates an "in-line" arrangement for recovering immunoglobulins in milk before the milk is subjected to normal processing. The unit comprises an inlet pipe 201 leading through a pre-filter 202 to a two-way valve 203. Pre-filter 202 can be an alternative to any pre-filter built into the immunoadsorbent column (feature 109 in FIG. 1) or can be used in conjunction with and such inbuilt pre-filter. From valve 203 pipes 204 and 205 lead respectively to immunoadsorbent columns 206 and 207. From the lower end of column 206 pipe 208 leads to a two-way valve 209 from which runs an outlet pipe 210 and a further pipe 211 leading via a two-way valve 212 to a conventional milk processing plant (not shown). Similarly, from the lower end of column 207 pipe 213 leads to a two way valve 214 from which runs an outlet pipe 215 and a further pipe 216 which connects with pipe 211 at valve 212.

The unit also comprises a mean for flushing each immunoadsorbent column and a means for eluting each column. The flushing means comprises a reservoir 217 for flushing medium linked via pipe 218 through pump 219 and pipe 220 which divides at junction 221 into a first arm leading 222 to inlet valve 223 in pipe 204 and a second arm 224 leading to inlet valve 225 in pipe 205.

The eluting means comprises a reservoir 226 for eluting medium with pipe 227 leading through pump 228 from which pipe 229 leads to junction 230 from which a first arm 231 leads to inlet valves 232 in pipe 204 and a second arm 233 leads to inlet valves 234 in pipe 205.

In operation, the immunoadsorbent columns 206 and 207 can be used alternately. Hence, for example, milk from a bulk tank (not shown) will be pumped through pipe 201 and pre-filter 202 down pipe 204 and through column 206. From column 206 the milk will flow through pipes 208 and 211 into the normal milk processing line. While the milk is passing through column 206 immunoglobulin material will be adsorbed by the immunoadsorbent. Meanwhile the second column 207 which has previously been saturated with immunoglobulin can be flushed free of milk using flushing medium from reservoir 217 and the flushing medium discarded through pipe 215. When the milk has been flushed from the column 207, the column can be eluted with eluting medium from reservoir 224. The eluate can also be collected from outlet pipe 215. When the eluting medium has removed a sufficient quantity of bound immunoglobulin from the immunoadsorbent the column can again be flushed with the flushing medium and is then ready for re-use. When column 206 has become saturated with immunoglobulin, the flow of milk can be diverted via valve 203 into the desaturated column 207. Initially, while the in-flowing milk is displacing the residual flushing medium in column 207, the liquid flowing out of column 207 can be discarded down pipe 215. When the residual flushing medium has been expelled from column 207 the pure milk can be diverted via valve 214 and pipe 216 into the milk processing line.

Although the unit has been depicted as comprising only two immunoadsorbent columns, it can be advantageous to employ a greater number of columns arranged in parallel. This would allow greater freedom of operation and more time for each individual column to be flushed and eluted before re-use.

FIG. 3 illustrates an alternative embodiment of the invention in which the recovery unit is incorporated as part of a recirculation system associated with a bulk tank. In a conventional milk processing plant, milk arriving at the plant is usually stored temporarily in a bulk tank before being transferred to the milk processing line. Associated with such bulk tanks it is normal to have a stirring or recirculating mechanism in order to reduce the risk of separation of the milk. In FIG. 3 a bulk tank 301 is connected via pipe 302 through pump 303 into a pre-filter 304 from which a pipe 305 leads via valves 306 and 307 into an immunoadsorbent column 308. Below column 308 a pipe 309 leads to a two-way valve 310 from which leads an outlet pipe 311 and a further pipe 312 returning to the bulk tank 301. The apparatus also comprises means for flushing and eluting column 307. From flushing medium reservoir 313 a pipe 314 leads via pump 315 to valve 306 in pipe 305. A reservoir 316 for eluting medium is connected via pipe 317 and pump 318 to valve 307. For simplicity this embodiment is shown as consisting of a single immunoadsorbent column 307 with its associated flushing and eluting facilities. In practice (as in the embodiment depicted in FIG. 2) a plurality of immunoadsorbent columns mounted in parallel will be more appropriate, thus allowing a saturated column to be flushed and eluted while one or more further columns are used to adsorb immunoglobulin. The essential operation of the unit as depicted in FIG. 3 is substantially identical to that described in relation to the unit shown in FIG. 2.

We claim:

1. A process for the recovery of immunoglobulins of high purity and potency from natural sources such as a milk and blood serum, characterised in that a source of immunoglobulins is contacted with an isoluble carrier material to which is bound a low-affinity monoclonal antibody specific to one or more of the immunoglobulins but not specific to any other common constituent of the source, the antibody binds immunoglobulin molecules and, following removal of the residue of the source, immunoglobulin molecules are released from the antibody.

2. A process for the recovery of immunoglobulins of high purity and potency from milk, characterised in that milk is contacted with an insoluble carrier material to which is bound a low-affinity monoclonal antibody specific to one or more milk immunoglobulins but not specific to any other common constituent of milk, the antibody binds immunoglobulin molecules and, following removal of the residue of the milk, immunoglobulin molecules are released from the antibody.

3. A process according to claim 1, characterised in that the monoclonal antibody is bound in an immunoadsorbent column or filter and release of the bound immunoglobulin is effected by eluting the immunoadsorbent column or filter.

4. A process according to claim 3, characterised in that the immunoadsorbent column or filter is flushed with a physiologically neutral liquid before being eluted.

5. A process according to claim 4, characterised in that the immunoadsorbent column or filter is flushed with a physiologically neutral liquid following elution but before re-use in adsorbing further immunoglobulin.

6. A process according to claim 1, characterised in that the source is bovine milk and the immunoglobulin recovered in bovine IgG$_1$.

* * * * *